(12) United States Patent
Satou et al.

(10) Patent No.: US 7,641,622 B2
(45) Date of Patent: Jan. 5, 2010

(54) GUIDE WIRE

(75) Inventors: Hideo Satou, Fujinomiya (JP); Katsuro Mishima, Yugawara-cho (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 82 days.

(21) Appl. No.: 11/905,818

(22) Filed: Oct. 4, 2007

(65) Prior Publication Data
US 2008/0194992 A1    Aug. 14, 2008

Related U.S. Application Data

(60) Provisional application No. 60/901,329, filed on Feb. 15, 2007.

(30) Foreign Application Priority Data
Feb. 9, 2007    (JP) ............... 2007-031315

(51) Int. Cl.
*A61B 5/00* (2006.01)
*A61M 25/00* (2006.01)
(52) U.S. Cl. .................................... 600/585
(58) Field of Classification Search ................ 600/585, 600/467; 604/532, 527
See application file for complete search history.

(56) References Cited

U.S. PATENT DOCUMENTS

| | | | |
|---|---|---|---|
| 4,925,445 A | 5/1990 | Sakamoto et al. | |
| 4,991,588 A * | 2/1991 | Pflueger et al. | ............. 600/467 |
| 5,069,226 A | 12/1991 | Yamauchi et al. | |
| 5,238,004 A | 8/1993 | Sahatjian et al. | |
| 5,269,759 A | 12/1993 | Hernandez et al. | |
| 5,345,945 A | 9/1994 | Hodgson et al. | |
| 5,368,049 A | 11/1994 | Raman et al. | |
| 5,373,619 A | 12/1994 | Fleischhacker et al. | |
| 5,402,799 A | 4/1995 | Colon et al. | |
| 5,411,476 A | 5/1995 | Abrams et al. | |
| 5,452,726 A | 9/1995 | Burmeister et al. | |
| 5,497,786 A | 3/1996 | Urick | |
| 5,498,250 A | 3/1996 | Prather | |
| 5,722,424 A | 3/1998 | Engelson | |
| 5,772,609 A | 6/1998 | Nguyen et al. | |
| 5,797,857 A | 8/1998 | Obitsu | |
| 5,876,356 A | 3/1999 | Viera et al. | |
| 5,924,998 A | 7/1999 | Cornelius | |
| 5,951,494 A | 9/1999 | Wang et al. | |
| 6,001,068 A | 12/1999 | Uchino et al. | |
| RE36,628 E | 3/2000 | Sagae et al. | |
| 6,093,157 A | 7/2000 | Chandrasekaran | |

(Continued)

FOREIGN PATENT DOCUMENTS

JP    10-146390 (A)    6/1998

*Primary Examiner*—Max Hindenburg
*Assistant Examiner*—Brian Szmal
(74) *Attorney, Agent, or Firm*—Buchanan Ingersoll & Rooney PC

(57) ABSTRACT

A guide wire includes an elongated flexible wire body and a tubular member disposed so as to cover the outer periphery of a portion of the wire body on the distal end side. The tubular member includes a lamination portion having an inner layer and an outer layer made of a resin material, and a reinforcing member disposed between the inner layer and the outer layer and formed by winding a wire material spirally. The reinforcing member reinforces the lamination portion.

27 Claims, 8 Drawing Sheets

U.S. PATENT DOCUMENTS

| | | |
|---|---|---|
| 6,165,292 A | 12/2000 | Abrams et al. |
| 6,234,981 B1 | 5/2001 | Howland |
| 6,306,105 B1 | 10/2001 | Rooney et al. |
| 6,390,992 B1 | 5/2002 | Morris et al. |
| 6,494,847 B1 | 12/2002 | Richardson et al. |
| 6,520,923 B1 | 2/2003 | Jalisi |
| 6,679,853 B1 | 1/2004 | Jalisi |
| 7,182,735 B2 | 2/2007 | Shireman et al. |
| 2004/0015151 A1* | 1/2004 | Chambers ................... 604/532 |
| 2004/0030266 A1 | 2/2004 | Murayama et al. |
| 2004/0039308 A1 | 2/2004 | Murayama et al. |
| 2004/0039309 A1 | 2/2004 | Murayama et al. |
| 2004/0167438 A1* | 8/2004 | Sharrow ..................... 600/585 |
| 2005/0152731 A1 | 7/2005 | Mishima et al. |

* cited by examiner

GUIDE WIRE

This application claims priority under 35 U.S.C. § 119(e) with respect to U.S. provisional Application No. 60/901,329 filed on Feb. 15, 2007, and is also based on and claims priority under 35 U.S.C. § 119(a) with respect to Japanese Application No. 2007-31315 filed on Feb. 9, 2007.

TECHNOLOGICAL FIELD

This invention generally relates to an interventional medical device. More particularly, the invention pertains to an interventional medical device in the form of a guide wire.

BACKGROUND DISCUSSION

A guide wire is employed to guide a catheter used for treatment of a region where surgical operation is difficult, for treatment where low-level intervention into the human body is desired, for inspection in cardiovascular contrast imaging and the like. For example, when PCI (Percutaneous Coronary Intervention) is performed, with the guide wire positioned so that its distal end is projecting from the distal end of a balloon catheter, the guide wire is inserted, under radioscopy, to a location in proximity to a constricted portion of a coronary artery which is a target region to guide the distal end portion of the balloon catheter to the location in proximity to the constricted portion.

An example of a guide wire for use with such treatment is described in U.S. Pat. No. 5,797,857. This guide wire includes a wire body (core member) having flexibility, a coil (X-ray contrast imaging metal coil) disposed so as to cover the outer periphery of the distal end portion of the wire body, and a coating layer (synthetic resin coating member, hydrophilic lubricating layer) for covering the outermost surface of the wire body and the coil.

When the guide wire disclosed in U.S. Pat. No. 5,797,857 is used to perform such an operation as described above, depending upon the state of the coronary artery such as the degree of the curvature of the coronary artery, a phenomenon such as described below sometimes occurs.

For example, if the guide wire is pushed in when the coil of the guide wire is positioned at (inserted in) a sharply bent portion of a coronary artery, excessive force (of such a degree that plastic deformation occurs) is sometimes applied to the coil. In this instance, part of a strand which forms the coil sometimes rides on an adjacent strand portion to cause plastic deformation of the coil. Therefore, there is the possibility that the coil may not be restored to its ordinary (normal) state and the pushing-in force from the proximal end portion of the wire body may not be transmitted with certainty to the distal end portion of the wire body through the coil. That is, the pushing-in performance may be significantly deteriorated.

Further, although the hydrophilic lubricating layer is provided on the coil of the guide wire of U.S. Pat. No. 5,797,857, depending upon the thickness of the guide wire, for example, when the distal end portion of the guide wire is positioned at (inserted in) a sharply bent portion of a coronary artery, comparatively high frictional resistance appears between the hydrophilic lubricating portion at the distal end portion and the bent portion described hereinabove. In other words, the hydrophilic lubricating layer at the distal end portion sometimes sticks to the bent portion. Therefore, there is the possibility that, even if torque is applied from the proximal end portion of the wire body, the torque may not be transmitted with certainty to the distal end portion of the wire body. That is, the torque transmission performance may be significantly deteriorated.

SUMMARY

According to one aspect, a guide wire includes an elongated flexible wire body and a tubular member disposed so as to cover the outer periphery of a portion of the wire body on the distal end side. The tubular member includes a lamination portion having an inner layer and an outer layer made of a resin material, and at least one wire member (wire-like member) disposed between the inner layer and the outer layer, with the wire member spaced from the wire body.

The wire member preferably serves to reinforce the lamination portion. The wire body preferably has, at a distal end portion thereof, a tapering portion whose outer diameter gradually decreases toward the distal end direction, and the proximal end of the tapering portion is surrounded by the tubular member. The tubular member is preferably fixed to the wire body either at the distal end of the wire member or at the distal end of the lamination portion. The wire member can possess a helical shape, and adjacent portions of the wire member can be spaced from each other. The wire member can also be a linear wire extending in a longitudinal direction of the tubular member. The wire member can also be in the form of a plurality of the linear wire members that are preferably disposed intermittently along a circumferential direction of the tubular member. The wire member preferably has, at part thereof, an exposed portion exposed from the distal end side and/or the proximal end side of the lamination portion.

According to another aspect, a guide wire comprises an elongated flexible wire body and a tubular member disposed so as to cover the outer periphery of a portion of the wire body on the distal end side. The tubular member is made of a resin material and includes a reinforcing member that reinforces at least a portion of the tubular member.

The tubular member preferably includes a lamination portion having an inner layer and an outer layer made of different materials, and at least the reinforcing member is disposed between the inner layer and the outer layer. The inner layer and the outer layer preferably have different mechanical characteristic properties from each other.

The guide wire can further include a coil disposed to cover the outer periphery of a portion of the wire body on the distal end side and formed in a spiral shape from a strand. The coil can overlap at least a part of the tubular member. The coil is preferably positioned on the distal end side of the tubular member.

The wide body preferably has, at a distal end portion thereof, a tapering portion whose outer diameter gradually decreases toward the distal end direction, and the boundary between the coil and the tubular member is positioned axially intermediately of the tapering portion in the longitudinal direction. The wire diameter of the strand of the coil and the thickness of the wall of the tubular member can be equal to each other. The wire diameter of the strand of the coil can also be greater than the wire diameter of the wire member.

According to another aspect, a guide wire comprises an elongated flexible wire body and a tubular member. The wire body possesses an outer periphery and portions of different outer diameter. The tubular member is disposed in covering relation to the outer periphery of the distal end portion of the wire body. The tubular member is axially positioned relative to the wire body to cover portions of the wire body which possess different outer diameters. The tubular member comprises a lamination portion made of resin material and a wire member. The tubular member possesses an inner surface spaced from the outer surface of the wire body with a gap between the inner surface of the tubular member and the outer surface of the wire body. The wire member is embedded in the resin material forming the lamination portion so that inner and outer surfaces of at least a portion of a longitudinal extent of the wire member are covered by the resin material.

BRIEF DESCRIPTION OF THE DRAWING FIGURES

The foregoing and additional features and aspects of the guide wire will become more apparent from the following detailed description considered with reference t the accompanying drawing figures briefly described below.

DETAILED DESCRIPTION

Figure 1:
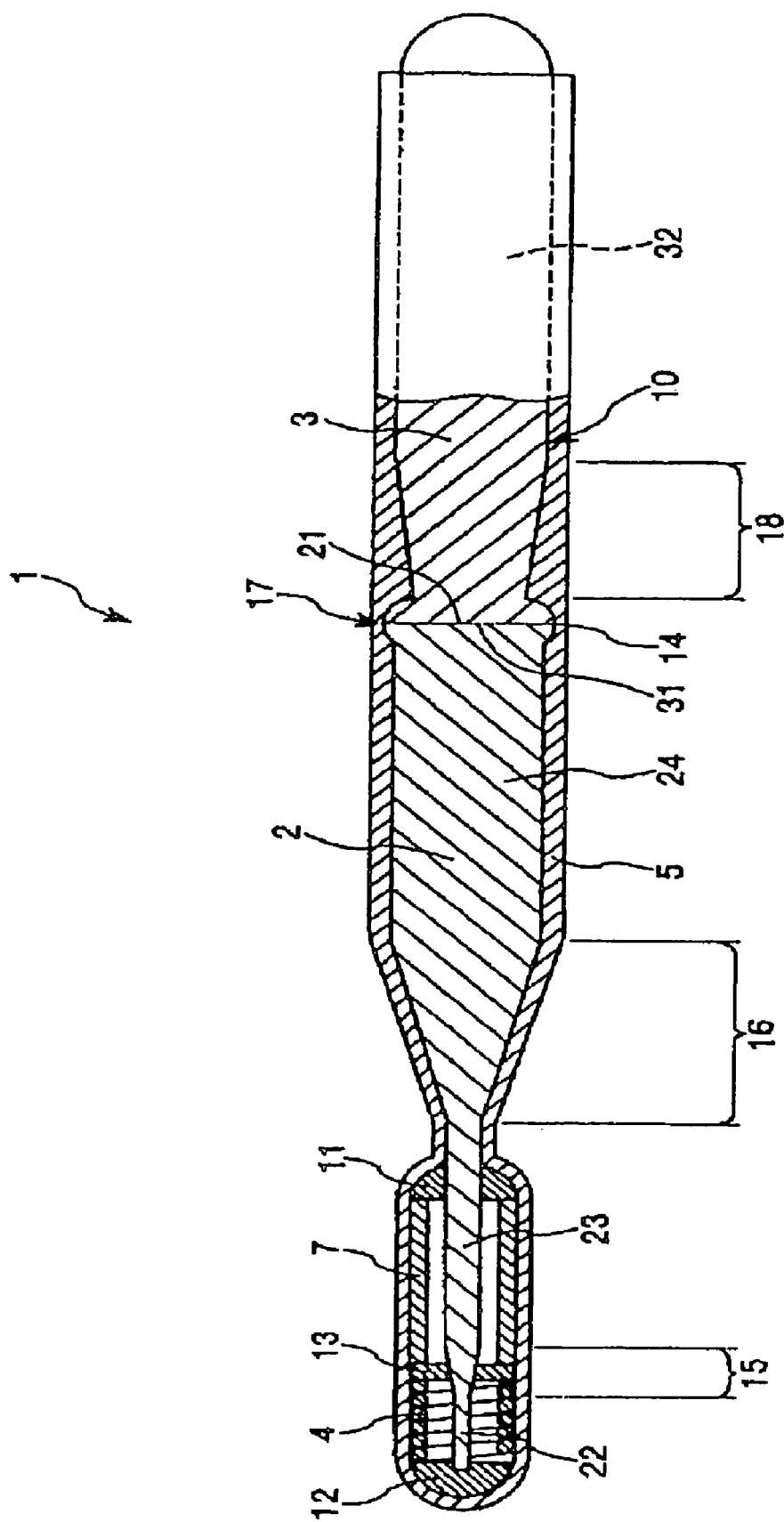
FIG. 1 is a view partly in section of a guide wire according to one embodiment disclosed herein.
Figure 2:
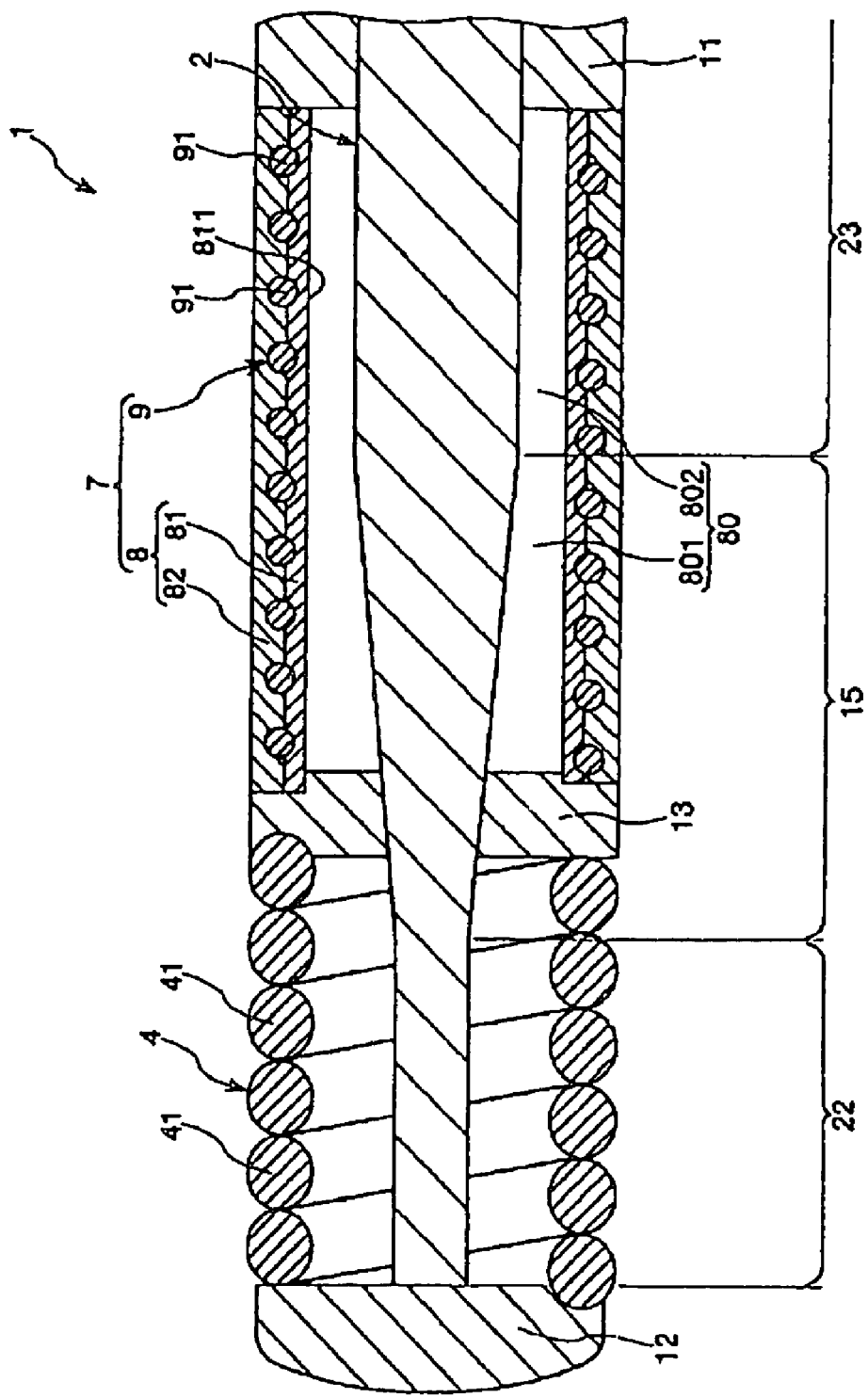
FIG. 2 is an enlarged view of a distal end portion of the guide wire shown in FIG. 1.

FIGS. 1 and 2 illustrate a guide wire according to a first embodiment. In the description below, the right side in FIGS. 1 and 2 (also in FIGS. 3 to 7 and 8) is referred to as the "proximal end" and the left side is referred to as the "distal end". In addition, in FIGS. 1 and 2 (also in FIGS. 3-8), to help facilitate an understanding of aspects and features of the guide wire, the guide wire is schematically shown as being contracted in the lengthwise direction and exaggerated in the thicknesswise direction. Thus, the illustrated dimensional ratio in the lengthwise direction and the thicknesswise direction is different from the actual ratio. Further, in FIG. 2 (similarly also in FIGS. 3 to 7), a coating layer which is depicted in FIG. 1 is omitted.

The guide wire 1 shown in FIG. 1 is a guide wire for a catheter and is adapted to be inserted in and used together with a catheter. The guide wire comprises a wire body 10, a coil 4 and a tubular member 7. The coil 4 and tubular member 7 cover the outer periphery of a portion of the wire body 10 on the distal end side. The wire body 10 is formed by connecting a first wire 2 disposed on the distal end side and a second wire 3 disposed on the proximate end side of the first wire 2 to each other. Although the total length of the guide wire 1 is not restricted to a particular length, it is preferably approximately 200 to 5000 mm.

The first wire 2 is a wire member having elasticity (flexibility). The length of the first wire 2 is not necessarily limited, though preferably ranges from approximately 20 to 1000 mm.

The first wire 2 comprises a small diameter portion 22, an outer diameter gradually decreasing portion (tapering portion) 15, a medium diameter portion 23, another outer diameter gradually decreasing portion 16, and a large diameter portion 24, and those portions 22, 15, 23, 16 and 24 are disposed in that order from the distal end side of the first wire 2 toward the proximal end side.

The large diameter portion 24 is a portion whose outer diameter is fixed or constant along the wire longitudinal direction.

The medium diameter portion 23 is disposed on the distal end side with respect to the large diameter portion 24. The medium diameter portion 23 is also a portion whose outer diameter is fixed or constant along the wire longitudinal direction, and the outer diameter of the medium diameter portion 23 is smaller than the outer diameter of the large diameter portion 24.

The small diameter portion 22 is disposed on the distal end side with respect to the medium diameter portion 23. The small diameter portion 22 is a portion whose outer diameter is constant or fixed along the wire longitudinal direction, and the outer diameter of the small diameter portion 22 is smaller than the outer diameter of the medium diameter portion 23.

Since the outer diameter of the first wire 2 decreases stepwise in the distal end direction in this manner, the rigidity (bending rigidity, torsional rigidity) of the first wire 2 can be reduced gradually toward the distal end direction. As a result, in the guide wire 1, good flexibility is obtained by the first wire 2, and the guide wire's follow-up performance along a blood vessel and the guide wire's safety are enhanced, and also undesired bending and so forth can be prevented.

The outer diameter gradually decreasing portion 15 is disposed between the small diameter portion 22 and the medium diameter portion 23. Further, the outer diameter gradually decreasing portion 16 is disposed between the medium diameter portion 23 and the large diameter portion 24. The outer diameter gradually decreasing portions 15, 16 are portions whose outer diameter gradually decreases in the distal end direction. The outer diameter gradually decreasing portion 15 is formed (connected) at the opposite ends thereof continuously to the small diameter portion 22 and the medium diameter portion 23. Also the outer diameter gradually decreasing portion 16 is formed (connected) at the opposite ends thereof continuously to the medium diameter portion 23 and the large diameter portion 24 substantially similarly to the outer diameter gradually decreasing portion 15.

Since such outer diameter gradually decreasing portions 15, 16 as described above are provided, the rigidity (bending rigidity, torsional rigidity) of the first wire 2 is decreased gradually toward the distal end direction by the outer diameter gradually decreasing portions 15, 16. As a result, effects such as those mentioned above associated with the outer diameter decrease are further enhanced.

Further, the tapering angle (reduction rate of the outer diameter) of the outer diameter gradually decreasing portions 15, 16 may be fixed or constant along the entirety of the portion 15, 16 in the wire longitudinal direction or may vary. For example, a portion in which the tapering angle (reduction rate of the outer diameter) is comparatively great and another portion in which the tapering angle is comparatively small may be formed alternately a plurality of times.

The component material for the first wire 2 is not specifically limited to a particular material as various metal materials such as, for example, stainless steel can be used. However, among such metal materials, alloys (including a superelastic alloy) which exhibit superelasticity are used preferably. More preferably, a superelastic alloy is used. A superelastic alloy is comparatively flexible and has restorability and hence does not fall into a bending habit readily. Therefore, if the first wire 2 is formed from a superelastic alloy, the guide wire 1 is provided at a portion on the distal end side thereof with sufficient elasticity and restorability against bending. As a result, the follow-up performance along a blood vessel which is curved or bent in a complicated manner is enhanced, and better operability is obtained. Further, even if the first wire 2 undergoes repetitive curving or bending deformation, a bending habit is not imparted thereto because of the restorability of the material. Thus deterioration of the operability caused by a bending habit imparted to the first wire 2 during use of the guide wire 1 can be inhibited or prevented.

Possible elastic (superelastic) metals which can be utilized include those elastic metals whose stress-distortion curve by tension has a variety of shapes, and also those elastic metals whose transformation temperature can or cannot be measured notably such as As (austenite start temperature), Af (austenite finish temperature), Ms (martensite start temperature), and Mf (martensite finish temperature) are included. Further, all of those superelastic metals which are deformed (distorted) by a great amount by stress and return to their original shape in response to removal of the stress are included. Thus, the superelastic alloy includes those which exhibit different tensile stress vs. strain curves (i.e., the superelastic alloys which can be used here are not limited to superelastic alloys having a particular tensile stress vs. strain curve), those which have transformation points such as As, Af, Ms, Mf, whether they are measurable clearly or not, and those which are largely deformed (strained) under stresses and return to their original shape upon removal of the stresses.

As a preferred composition of the superelastic alloy, Ni—Ti-based alloys such as a Ni—Ti alloy containing Ni by 49 to 52 atom %, a Cu—Zn alloy containing Zn by 38.5 to 41.5 weight %, Cu—Zn—X alloys (X is at least one of Be, Si, Sn, Al, and Ga) containing X by 1 to 10 weight %, a Ni—Al alloy containing Al by 36 to 38 atom %, and so forth may be used. Among them, the Ni—Ti-based alloys described above are particularly preferable. It is to be noted that the superelastic alloy represented by Ni—Ti-based alloys is excellent also in adhesive property of a coating layer 5 hereinafter described.

The second wire 3 is connected (coupled) at the distal end thereof to the proximal end of the first wire 2 by welding. The second wire 3 is a wire member having elasticity. The length of the second wire 3 is not restricted to a particular value, though preferably it ranges approximately from 20 to 4800 mm.

The second wire 3 has an outer diameter gradually decreasing portion 18 disposed in the proximity of the distal end of the second wire 3, and an outer diameter fixed portion 32 disposed adjacent the proximal end side of the outer diameter gradually decreasing portion 18. Thus, the outer diameter gradually decreasing portion 18 is positioned distally of the outer diameter fixed portion 32.

The outer diameter gradually decreasing portion 18 is a portion whose outer diameter gradually decreases in the distal end direction. Meanwhile, the outer diameter fixed portion 32 is a portion whose outer diameter is fixed along the wire longitudinal direction, and the outer diameter thereof is equal to the outer diameter of the proximal end of the outer diameter gradually decreasing portion 18.

In the second wire 3 having the configuration described above and shown in FIG. 1, the outer diameter fixed portion 32 is higher in rigidity than the outer diameter gradually decreasing portion 18. Consequently, an effect is achieved in which the elasticity varies smoothly between the first wire 2 and the second wire 3.

The second wire 3 is made of a material having elastic moduli (Young's modulus [modulus of longitudinal elasticity], modulus of torsion [modulus of transverse elasticity], modulus of elasticity of volume) higher than those of the component material of the first wire 2. Consequently, the second wire 3 possesses suitable rigidities (bending rigidity, torsional rigidity), thus making the guide wire 1 tough. Consequently, the pushing-in property and the torque transmission property are enhanced and relatively superior insertion operability is obtained.

The component material (raw material) of the second wire 3 is not specifically limited, and various metal materials such as stainless steel (all sorts of SUS such as, for example, SUS304, SUS303, SUS316, SUS316L, SUS31LJ1, SUS316J1L, SUS405, SUS430, SUS434, SUS444, SUS429, SUS430F, and SUS302), piano wires, cobalt-based alloys, and anelastic alloys can be used.

A wire formed from the cobalt-based alloys possesses a relatively high elastic modulus and has a suitable elastic limit. Therefore, the second wire 3 when formed from a cobalt-based alloy has a particularly excellent torque transmission property and suffers relatively little from the problem of buckling and the like. Although any cobalt-based alloy may be used only if it contains Co as a component element, preferably a cobalt-based alloy which contains Co as a main component (Co-base alloy: an alloy in which the content of Co is highest in weight ratio among elements which compose the alloy) is used. More preferably, a Co—Ni—Cr-based alloy is used. Since an alloy having such a composition as described above is used as a component material for the second wire 3, the effects described above become further enhanced. Further, since an alloy having such a composition as described above has a high elastic modulus and such a high elastic limit as to allow cold forming, miniaturization can be achieved while inhibiting or preventing the occurrence of buckling, and the guide wire can be provided with rigidity suitable for insertion into a predetermined portion.

The end portions of the first wire 2 and the second wire 3 are joined to each other. In the guide wire 1 shown in FIG. 1, the proximal end face of the first wire 2 and distal end face of the second wire 3 are joined together by welding and a welded portion 14 is formed on the boundary between the two wires.

The method for welding the first wire 2 and the second wire 3 is not restricted particularly. For example, spot welding using a laser, butt resistance welding such as butt seam welding, and so forth are possible alternatives, though butt resistance welding is preferably used. The welded portion 14 is provided with higher coupling strength.

Further, in this illustrated embodiment, a protrusion 17 which protrudes toward an outer circumferential direction is formed at the welded portion 14. By virtue of this protrusion 17, a relatively large joining area is provided between the first wire 2 and the second wire 3, and particularly high joining strength is obtained between the first wire 2 and the second wire 3. Consequently, with this guide wire 1, torsional torque or pushing-in force from the second wire 3 is transmitted with a higher degree of certainty to the first wire 2.

Further, with the protrusion 17, it is possible to visually observe the welded portion 14 between the first wire 2 and the second wire 3 with a higher degree of ease, for example, under radioscopy. As a result, by confirming a radioscopic image, the advancing situation or position of the guide wire 1 or the catheter in a blood vessel or the like can be readily ascertained and with relative certainty. This can contribute to reduction of the operation time and enhancement of the security.

The method of forming the protrusion 17 is not particularly limited. The following methods can be applied.

Butt seam welding is preferably used as the welding for the first wire 2 and the second wire 3. In this instance, while a predetermined voltage is applied to the first wire 2 and the second wire 3 by a butt welding machine, a connection end face 21 of the first wire 2 on the proximal end side and a connection end face 31 of the second wire 3 on the distal end side contact each other under pressure. By virtue of this pressurized contact, a melt layer is formed at the contact portion so that the first wire 2 and the second wire 3 are connected firmly to each other.

Further, a projecting portion is formed at the connecting portion (welded portion 14) deformed by the pressurized contact. The protrusion 17 can also be formed by shaping the projecting portion so as to be moderated.

As shown in FIGS. 1 and 2, the outer periphery of a distal end portion (portion on the distal end side) of the first wire 2 (wire body 10) is covered with the coil 4 and the tubular member 7. In the illustrated embodiment of the guide wire 1, the coil 4 is disposed on the distal end side of the first wire 2, and the tubular member 7 is disposed on the proximal end side adjacent the coil 4 (i.e., the tubular member 7 is disposed proximally of the coil 4). The coil 4 and the tubular member 7 disposed in this manner cover the first wire 2 such that the coil 4 covers a portion of the first wire 2 from the distal end of the small diameter portion 22 to an intermediate portion of the outer diameter gradually decreasing portion 15, while the tubular member 7 covers another portion of the first wire 2 from the intermediate portion of the outer diameter gradually decreasing portion 15 to an intermediate portion of the medium diameter portion 23. Stated differently, the coil 4 and the tubular member 7 cover a portion of the first wire 2 located distally of the outer diameter gradually decreasing portion 16.

The coil 4 is a member formed from a wire member (strand) 41 wound spirally. In the configuration shown in FIGS. 1 and 2, a portion (small diameter portion 22 and outer diameter gradually decreasing portion 15) of the first wire 2 on the distal end side is fitted at a substantially central portion on the inner side of the coil 4. Further, the distal end side portion of the first wire 2 is fitted in a non-contacting relationship with the inner surface of the coil 4 (i.e., a space or gap exists between the outer surface of the first wire 2 and the inner surface of the coil 4).

In the configuration of the guide wire shown in FIGS. 1 and 2, when no external force is applied to the coil 4, the adjacent spirally wound portions of the wire member 41 contact each other. In other words, the wire member 41 is wound closely without gap between adjacent turns or windings. It is to be noted that the spirally wound portions of the wire member 41 are not restricted to such close arrangement without a gap. Indeed, the coil 4 can be configured so that a gap exists between adjacent spirally wound portions of the wire member 41.

The coil 4 is preferably made of a metal material. As the metal material used to form the coil 4, for example, stainless steel, superelastic alloys, cobalt-based alloys, noble irons such as gold, platinum, and tungsten and alloys containing any of them may be used. Particularly where the coil 4 is made of an X-ray impermeable material such as a noble metal, a radioscopic property is provided to the guide wire 1, and it is possible to insert the guide wire 1 into a living organism while the position of the distal end portion is confirmed under radioscopy, which is preferable.

The coil 4 is fixed at a distal end portion thereof to the distal end of the small diameter portion 22 of the first wire 2 by a fixing material 12, and is fixed at a proximal end portion thereof to an intermediate portion of the outer diameter gradually decreasing portion 15 by another fixing material 13. The fixing materials 12, 13 (similar also to a fixing material 11 hereinafter described) are each formed from solder (wax). It is to be noted that the fixing materials 12 and 13 are not limited to solder, but may be a bonding agent. Further, the fixation method of the coil 4 is not limited to that which uses a fixing material but may be, for example, welding. Further, in order to inhibit or prevent damage to the inner surface of a blood vessel, the distal end face of the fixing material 12 is preferably somewhat rounded.

Where the coating layer 5 is omitted from the guide wire 1, the first wire 2 is covered with the coil 4 and has a reduced contact area with, for example, a catheter. Consequently, the sliding resistance is reduced and so the operability of the guide wire 1 is further enhanced.

Further, in the case of this illustrated and described embodiment, while the wire member 41 used in the coil 4 has a circular transverse cross-section, the cross section of the wire member 41 is not limited to this. For example, the wire member 41 may have an elliptical transverse cross-sectional shape, a quadrangular transverse cross-sectional shape (particularly a rectangular cross-sectional shape), or the like.

As best illustrated in FIG. 2, the tubular member 7 positioned on the proximal end side of the coil 4 includes or comprises a lamination portion 8 having an inner layer 81 and an outer layer 82, both made of a resin material, and a reinforcing member or wire member (inclusive of wire-like member) 9 disposed between the inner layer 81 and the outer layer 82. A portion of the first wire 2 (outer diameter gradually decreasing portion 15 and medium diameter portion 23) on the distal end side extends along a central portion of the tubular member 7 in a manner similar to the coil 4. Further, the inner circumferential surface 811 (the inner layer 81) of the tubular member 7 is held out of contact with (i.e., is spaced from) the outer circumferential surface of the portion of the second wire which the tubular member surrounds or encircles.

The lamination portion 8 has a tubular (pipe-shaped) general profile. The inner layer 81 is disposed on the inner side of the lamination portion 8 while the outer layer 82 is disposed (laminated) on the outer side, on the outer side of the inner layer 81.

The surface of the outer layer 82 has a substantially even surface of equal outer diameter (constant outer diameter) from the proximal end to the distal end. However, the outer layer 82 may have an uneven surface along an uneven geometry of the reinforcing member 9. Where the surface of the outer layer 82 has an uneven surface, sliding properties are enhanced.

The component material (resin material) of the inner layer 81 and the outer layer 82 is not limited to specific materials. However, as examples, polyolefin such as polyethylene, polypropylene, ethylene-propylene copolymer, ethylene-vinyl acetate copolymer, and crosslinked ethylene-vinyl acetate copolymer, polyvinyl chloride, polyester (PET, PBT, PEN, and so forth), polyamide, polyimide, polyurethane, polystyrene, polycarbonate, fluorocarbon resins (polytetrafluoroethylene and so forth), silicone resins, silicone rubber, other various kinds of elastomer (for example, thermoplastic elastomer of the polyurethane type, the polyamide type, the polyester type, and so forth), and so forth may be used. The materials mentioned may be used individually or in combinations of two or more materials.

Also, the inner layer 81 and the outer layer 82 may be formed from the same component material or from component materials different from each other.

Where the inner layer 81 and the outer layer 82 are formed from the same component material, the two layers mutually dissolve or integrate with one another upon molding of the tubular member 7 so that they can hold the reinforcing member 9 firmly.

Where the inner layer 81 and the outer layer 82 are formed from different component materials from each other, materials having different rigidities (bending rigidity, torsional rigidity) may be used. For example, in the case of the configuration shown in FIG. 2 in which the thickness of the inner layer 81 is smaller than the thickness of the outer 82, by forming the outer layer 82 from a material whose rigidity is higher than that of the inner layer 81, a distal end portion of the guide wire 1 can be provided with relatively high rigidity. Consequently, when the guide wire 1 is to be inserted into a catheter or a living organism, inadvertent deformation (bending) can be prevented from occurring at a distal end portion of the guide wire 1. In other words, the guide wire 1 possesses excellent kink resistance. Further, since inadvertent deformation of a distal end portion of the guide wire 1 is prevented, that is since a normal state of a distal end portion is maintained, the guide wire 1 can be impelled readily and with high reliability. In other words, the guide wire 1 possesses quite good pushing-in performance characteristics.

Further, where the component materials of the inner layer 81 and the outer layer 82 are different from each other, the inner layer 81 may be made of a material such as, for example, polytetrafluoro-ethylene, fluorinated ethylene-propylene (FEP), or high density polyethylene, and the outer layer 82 may be made of, for example, polyurethane elastomer, polyamide elastomer, polyester elastomer, or the like. Where a distal end portion of the guide wire 1 is bent when the guide wire 1 is operated, while part of the inner layer 81 and a part of the first wire 2 may contact each other and friction may occur between them, the friction is reduced by an action by the component material of the inner layer 81 described above. Consequently, the bending of the distal end portion of the guide wire 1 is performed relatively smoothly. Further, by virtue of the characteristics of the component material of the outer layer 82 as described above, a hydrophilic material (coating layer 5) which is discussed in more detail below can be relatively readily fixed to the outer layer 82.

In this manner, the lamination portion 8 (guide wire 1) can be configured such that the inner layer 81 and the outer layer 82 have different mechanical characteristics (rigidity, coefficient of friction, and so forth) from each other.

As mentioned, the reinforcing member 9 is disposed between the inner layer 81 and the outer layer 82. In the illustrated embodiment, the wire member or reinforcing member 9 is embedded in the lamination portion 8 so that the material forming the lamination portion extends both radially inwardly and radially outwardly of the wire member 9. Thus, the inner and outer surfaces of wire member 9 are covered by the resin material forming the lamination portion 8. The reinforcing member 9 reinforces the lamination portion 8. Since the reinforcing member 9 has such a function (reinforcing function), the rigidity of the entire tubular member 7 against compression can be maintained with relative reliability. Consequently, when the guide wire 1 is inserted into a catheter or a living organism, the tubular member 7 exhibits enhanced kink resistance.

Further, when the distal end portion of the guide wire 1 is positioned (inserted) in a blood vessel which is bent sharply such as, for example, a coronary artery, the distal end portion sometimes sticks (adheres closely) to the wall of the blood vessel. Also, in such an instance as just described, since, at the distal end portion of the guide wire 1, the first wire 2 (wire body 10) is supported for turning motion to some degree (has some degree of freedom) with respect to the tubular member 7, torque from the proximal end side of the guide wire 1 is transmitted with reliability to the distal end through a portion of the first wire 2 which is covered with the tubular member 7 (similar also with the coil 4). In other words, the guide wire 1 is excellent in torque transmission property.

In the present embodiment, the reinforcing member 9 is wound spirally in a concentric relationship with the lamination portion 8 as shown in FIG. 2. With the reinforcing member 9 having such a shape as just described, the lamination portion 8 can be reinforced generally uniformly in the longitudinal direction thereof and can be reinforced generally uniformly also in the circumferential direction. Consequently, the circularity of the entire tubular member 7, or the ability of the tubular member 7 to maintain its (circular) shape is enhanced, and the torque transmission property is enhanced.

The reinforcing member 9 may be a wire strand tube covered with the outer layer 82.

Further, in the spiral reinforcing member 9, adjacent portions (windings) of a wire material 91 are spaced away from each other. Consequently, while the rigidity of the tubular member 7 is maintained, when the guide wire 1 is operated, the tubular member 7 can be bent rather readily in accordance with the degree of bending, for example, of a blood vessel. It is to be noted the spiral reinforcing member 9 can be configured so that adjacent portions (windings) of the wire material 91 contact each other.

While the component material forming the reinforcing member 9 (wire material 91) is not restricted, a component material similar to that of the coil 4 may be used by way of example. Where the coil 4 is made of an X-ray impermeable material, the reinforcing member 9 is preferably made of a material having a higher strength than that of the coil 4.

In the illustrated embodiment, the wire material 91 of the reinforcing member 9 possesses a circular cross-sectional shape. However, the cross-section of the wire member 41 may be, for example, an elliptical shape, a quadrangular shape (particularly a rectangular shape), or the like.

As seen in FIG. 2, the tubular member 7 is fixed at the distal end portion (of the lamination portion 8) thereof to an intermediate portion of the outer diameter gradually decreasing portion 15 of the first wire 2 by the fixing material 13 and is also fixed at a proximal end portion thereof to an intermediate portion of the medium diameter portion 23 with the fixing material 11. With these fixations, the tubular member 7 is fixed with relatively high reliability to the wire body 10. In the embodiment shown in FIGS. 1 and 2, the fixing material 13 serves to fix the coil 4 and also the tubular member 7.

The tubular member 7 having a configuration such as described above is spaced away from the first wire 2 as described previously and so a gap 80 is formed between the tubular member 7 and the first wire 2. Consequently, when the distal end portion (portion on the distal end side) of the wire body 10 is bent, the deformation is performed readily and relatively smoothly.

The gap 80 is divided, at the boundary between the outer diameter gradually decreasing portion 15 and the medium diameter portion 23, into a gap 801 on the distal end side (outer diameter gradually decreasing portion 15 side) and another gap 802 on the proximal end side (medium diameter portion 23 side).

In a guide wire in which the outer periphery of the distal end portion of the wire body is entirely covered with a coil, where such an outer diameter gradually decreasing portion 15 as in the guide wire 1 of the present invention is formed, the coil sometimes suffers from inadvertent deformation at the gap 801. This inadvertent deformation can be a deformation resulting from a winding(s) of the coil riding on the adjacent winding, with this state being maintained, that is plastic deformation.

However, in the illustrated guide wire 1 described above, since the tubular member 7 defines the gap 801 with respect to the wire body 10, such inadvertent deformation as described above can be avoided with a relatively high degree of reliability. Consequently, the guide wire 1 can be used in a normal state. In other words, the pushing-in force can be transmitted with a high degree of reliability to the distal end of the guide wire 1.

Further, since the gap 80 is formed, the degree of freedom in turning portion of the first wire 2 around the center axis with respect to the tubular member 7 is assured with certainty. In other words, the first wire 2 can be turned around the center axis because the first wire 2 is not totally connected with the entirety of the tubular member 7. Consequently, even if a situation should arise where the distal end portion of the guide wire 1 sticks to the wall of a blood vessel, torque from the proximal end side of the guide wire 1 is transmitted with a higher degree of certainty to the distal end of the guide wire 1.

Further, since the proximal end of the outer diameter gradually decreasing portion 15 is positioned inside the tubular member 7, the rigidity of the entire guide wire 1 (including both the wire body 10 and the tubular member 7) can be reduced gradually from the proximal end of the outer diameter gradually decreasing portion 15 toward the distal end direction. Consequently, the guide wire 1 is provided at a distal end portion thereof with good flexibility, resulting in enhancement of the follow-up ability of the guide wire along a blood vessel, safety, prevention of bending, and so forth.

As described hereinabove, in the guide wire 1, the coil 4 and the tubular member 7 are secured intermediately (axially) of the outer diameter gradually decreasing portion 15 by the fixing material 13. Therefore, the boundary between the coil 4 and the tubular member 7 is positioned intermediately (axially) of the outer diameter gradually decreasing portion 15. Consequently, the effect that inadvertent deformation of the coil 4 is inhibited is enhanced.

As shown in FIG. 2, the outside wire diameter of the wire member 41 forming the coil 4 is equal to the thickness of a wall portion of the tubular member 7 (i.e., the sum of the thickness of the inner layer 81 and the thickness of the outer layer 82). Further, the wire diameter of the wire member 41 is greater than the wire diameter of the wire material 91 of the reinforcing member 9.

With the wire diameter of the wire member 41 set in this manner, the radioscopic property of the coil 4 is increased. By decreasing the wire diameter of the wire material 91, the thickness of the wall of the tubular member 7 is reduced.

The method for fabricating the tubular member 7 is not limited to a particular method. Set forth below is a description of one method which can be employed.

First, an inner layer 81 is installed on an outer peripheral portion of a core member. The inner layer 81 is formed, for example, by applying solution which contains a component material for the inner layer 81 to an outer peripheral portion of the core member (or immersing the core member in such solution) and drying the solution. Before the solution which contains the component material for the inner layer 81 is dried, a wire material 91 is wound spirally on the solution that is on the outer peripheral portion of the core member. In this state, the solution is dried.

An outer layer 82 is produced as a hollow pipe member, for example by hollow extrusion molding or wire coating molding, preferably by hollow extrusion molding. The thickness and the length of the pipe member are set to predetermined dimensions in advance.

Then, the pipe member is fitted on the core member on which the inner layer 81 and the reinforcing member 9 described above are provided.

Thereafter, a heat-shrinkable tube made of, for example, a fluorocarbon resin is fitted on the outer layer 82 (pipe member) and is heated so as to thermally shrink. Consequently, the material which forms the outer layer 82 is melted and integrated with (joined to) the inner layer 81 and the reinforcing member 9. Thereafter, the heat-shrinkable tube is removed. Before or after this, the core member is pulled out. The result is the tubular member 7 as described above.

As shown in FIG. 1, the coating layer 5 for covering the entirety (or part) of the guide wire 1 is provided on the outer surface of the guide wire 1. While the coating layer 5 can be formed for various purposes, it sometimes reduces the friction (sliding resistance) of the guide wire 1 to help improve the sliding performance and thereby enhance the operability of the guide wire 1.

In order to achieve reduction of the friction (sliding resistance) of the guide wire 1, the coating layer 5 is preferably made a material which can reduce the friction as described below. The frictional resistance (sliding resistance) with the inner wall of a catheter which is used together with the guide wire 1 is thereby reduced to enhance the sliding performance, and so the operability of the guide wire 1 in the catheter becomes better. Further, as the sliding resistance of the guide wire 1 decreases, when the guide wire 1 is moved and/or turned in the catheter, kink (bend) or torsion of the guide wire 1, particularly kink or torsion in the proximity of the welded portion 14, is inhibited or prevented with a higher degree of certainty.

Materials which can be used to reduce friction as described above include, for example, polyolefin such as polyethylene and polypropylene, polyvinyl chloride, polyester (PET, PBT, and so forth), polyamide, polyimide, polyurethane, polystyrene, polycarbonate, silicone resins, fluorocarbon resins (PTFE, ETFE, and so forth), or composites (combinations) of these materials.

Further, the coating layer 5 may be provided to achieve enhancement of the safety when the guide wire 1 is inserted into a blood vessel or the like. To this end, the coating layer 5 is preferably made of a material (soft material, resilient material) having relatively high flexibility.

Examples of materials which has such relatively high flexibility as described above include polyolefin such as polyethylene and polypropylene, polyvinyl chloride, polyester (PET, PBT, and so forth), polyamide, polyimide, polyurethane, polystyrene, silicone resins, thermoplastic elastomer such as polyurethane elastomer, polyester elastomer and polyamide elastomer, various rubber materials such as latex and silicone rubber, and composite materials each in the form of a combination of two or more of the aforementioned materials.

It is to be noted that the coating layer 5 may be in the form of a single layer or a laminate of two or more layers.

Further, a hydrophilic material is preferably coated on the outer surface, at least at the distal end portion, of the guide wire 1. The hydrophilic material, when wetted, provides lubricity and results in reduction of the friction (sliding resistance) of the guide wire 1 and enhancement of the sliding performance. Accordingly, the operability of the guide wire 1 is enhanced.

Examples of the hydrophilic material include cellulose-based high-molecular substances, polyethylene oxide-based high-molecular substances, maleic anhydride-based high-molecular substances (for example, such maleic anhydride copolymer as methyl vinyl ether-maleic anhydride copolymer), acrylamide-based high-molecular substances (for example, block copolymer of polyacrylamide, polyglycidymethacrelate-dimethylacrylamide (PGMA-DMAA)), water-soluble nylon, polyvinyl alcohol, polyvinyl pyrrolidone, and so forth are available.

Such hydrophilic materials in most cases exhibit lubricity by wetting (water absorption) and reduce the frictional resistance (sliding resistance) with the inner wall of a catheter used together with the guide wire 1. Consequently, the sliding performance of the guide wire 1 is enhanced and the operability of the guide wire 1 in the catheter is improved.

The coating layer 5 may be omitted at the distal end portion of the guide wire 1 (the portion at which the coil 4 and the tubular member 7 are disposed). In this instance, although the outer layer 82 tends to be exfoliated, for example by the sliding contact (resistance) with the inner circumferential surface of the catheter, part of the reinforcing member 9 extends in the outer layer 82. Consequently, the joining strength between the outer layer 82 and the inner layer 81 and the reinforcing member 9 is increased and so the exfoliation is prevented with relative reliability.

Figure 3:
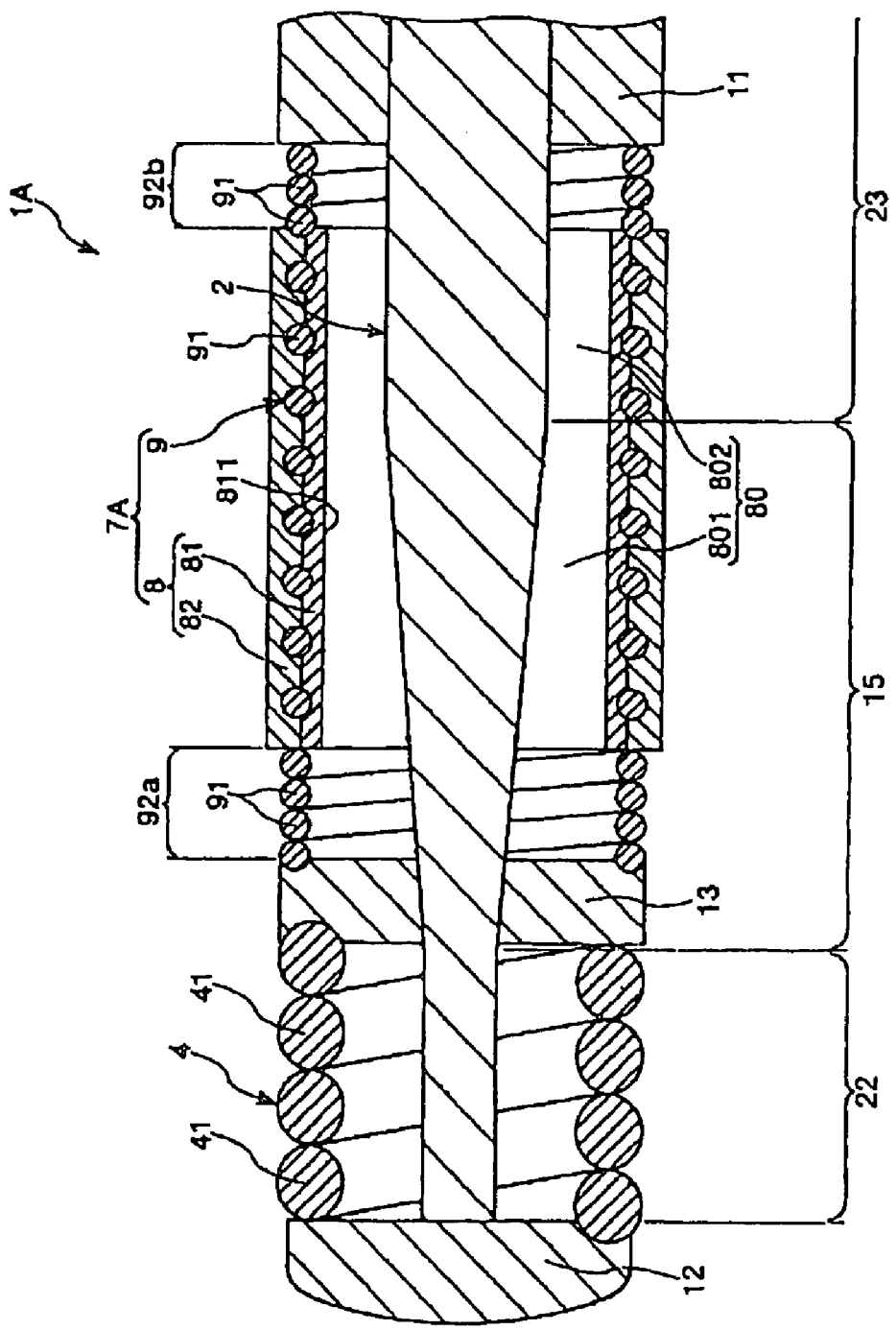
FIG. 3 is an enlarged detailed view of a distal end portion of a guide wire according to a second embodiment.

FIG. 3 illustrates the distal end portion of a guide wire according to a second embodiment. The description below of the guide wire according to this second embodiment will primarily address aspects of the guide wire different from those associated with the first embodiment. Features of the second embodiment similar to those in the first embodiment are identified by the same reference numeral and a detailed description of such features is not repeated. This second embodiment is similar to the first embodiment described above and shown in FIGS. 1 and 2, except that the configuration of the tubular member in the second embodiment is different.

In the tubular member 7A of the guide wire 1A shown in FIG. 3, the reinforcing member 9 is exposed from the distal end side and the proximal end of the lamination portion 8. The exposed portion of the reinforcing member 9 on the distal end side is hereinafter referred to as the exposed portion 92a, and the portion of the reinforcing member 9 on the proximal end side is hereafter referred to as the exposed portion 92b.

The exposed portion 92a of the tubular member 7 (the distal end portion of the tubular member) is fixed to the wire body 10 through the fixing material 13 and the exposed portion 92b of the tubular member 7 (the proximal end portion of the tubular member) is fixed to the wire body 10 through the fixing material 11.

The exposed portions 92a, 92b are formed spirally similarly to the portion of the reinforcing member 9 integrated or embedded in the lamination portion 8. Further, at the exposed portions 92a, 92b, adjacent portions or windings of the wire material 91 contact each other.

With the guide wire 1A having the configuration described above, since the exposed portions 92a and 92b are not covered with the lamination portion 8, the degree of freedom in the turning motion of the first wire 2 (wire body 10) around a center axis with respect to the tubular member 7A is relatively assured with a higher degree of certainty by the exposed portions 92a and 92b. Consequently, even if, for example, the distal end portion of the guide wire 1A should stick to the wall of a blood vessel, when torque is applied from the proximal end side of the guide wire 1A, the torque arrives at or is transmitted to the distal end portion of the guide wire 1A with a higher degree of reliability through the small diameter portion 22 from an intermediate portion of the outer diameter fixed portion 32.

In addition, the exposed portions 92a, 92b as described above individually function as a buffering portion (buffer) for securing the degree of freedom of the first wire 2 with a higher degree of accuracy, that is, for buffering excessive fixation from the outside to a distal end portion of the guide wire 1A.

In the illustrated embodiment, the adjacent windings of the exposed portions 92a, 92b of the wire material 91 contact each other. However, the arrangement of the exposed portions 92a, 92b is not limited in this regard as adjacent portions of the wire material 91 may be spaced from each other. Further, the exposed portions 92a, 92b may be configured such that adjacent portions (windings) of the wire material 91 on one of the exposed portions 92a or 92b contact each other while adjacent portions (windings) of the wire material 91 on the other one 92b or 92a are spaced from each other.

Figure 4:
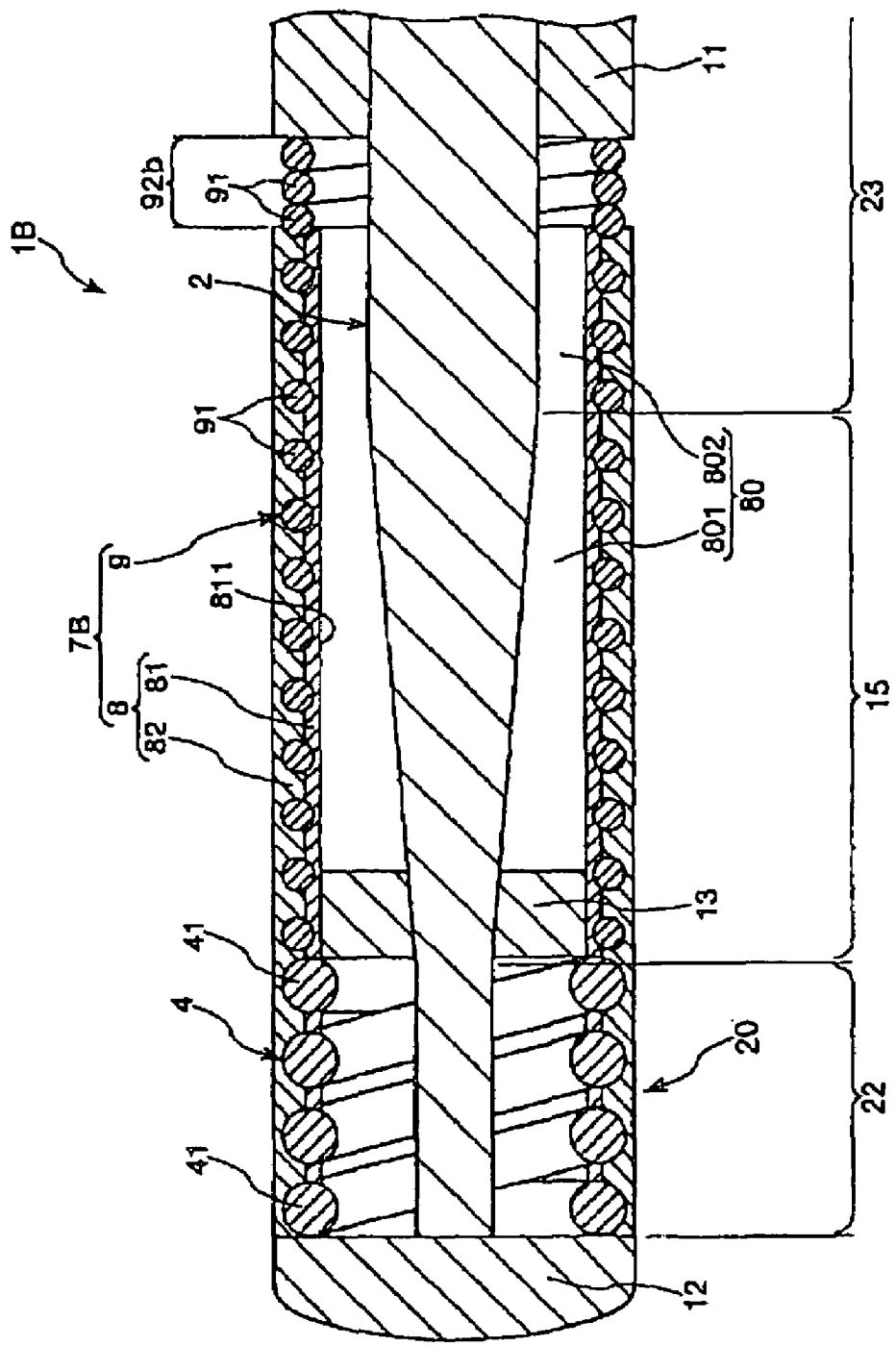
FIG. 4 is an enlarged detailed view of a distal end portion of a guide wire according to a third embodiment.

FIG. 4 illustrates the distal end portion of a guide wire according to a third embodiment. The description below of the guide wire according to this third embodiment will primarily discuss aspects of the guide wire different from those associated with the embodiments described above. Features of the third embodiment similar to those in the earlier embodiments are identified by the same reference numeral and a detailed description of such features is not repeated. This third embodiment is similar to the second embodiment described above, except that the third embodiment differs with respect to the installation state of the tubular member and the coil.

In the guide wire 1B shown in FIG. 4, the tubular member 7B covers a portion of the first wire 2 from the distal end of the small diameter portion 22 to an intermediate portion of the medium diameter portion 23. The distal end portion of the tubular member 7B (distal end of the lamination portion 8) is fixed to the distal end of the small diameter portion 22 through the fixing material 12, and the proximal end portion of the tubular member 7B (proximal end of the exposed portion 92b) is fixed to an intermediate portion of the medium diameter portion 23 through the fixing material 11. Further, the tubular member 7B is fixed at an intermediate portion of the inner side thereof to an intermediate portion of the outer diameter gradually decreasing portion 15 of the first wire 2 through the fixing material 13.

In the tubular member 7B as described above, the reinforcing member 9 extends in the proximal end direction from an intermediate portion of the outer diameter gradually decreasing portion 15. The coil 4 is disposed at a portion of the tubular member 7B (lamination portion 8) at which the reinforcing member 9 is not disposed. In particular, the coil 4 is supported on (fixed to) a portion of the tubular member 7B (lamination portion 8) at which the reinforcing member 9 is not disposed (i.e., the coil 4 and the reinforcing member 9 do not axially overlap one another). An overlapping portion 20 is formed at which the tubular member 7B and the coil 4 overlap, and this overlapping portion 20 is formed at the distal end portion of the guide wire 1B.

By virtue of the overlapping portion 20, the rigidity of the most distal end portion of the guide wire 1B can be set higher than the rigidity of the most distal end portion of the guide wire of, for example, the first embodiment. Consequently, the structure can be maintained even if torque is applied frequently.

In the illustrated construction of the guide wire shown in FIG. 4, the exposed portion 92b of the reinforcing member 9 is positioned on the proximal end side of the lamination portion 8. However, the guide wire is not limited in this regard as the exposed portion may be positioned (corresponding to the exposed portion 92a) on the distal end side of the lamination portion 8.

Figure 5:
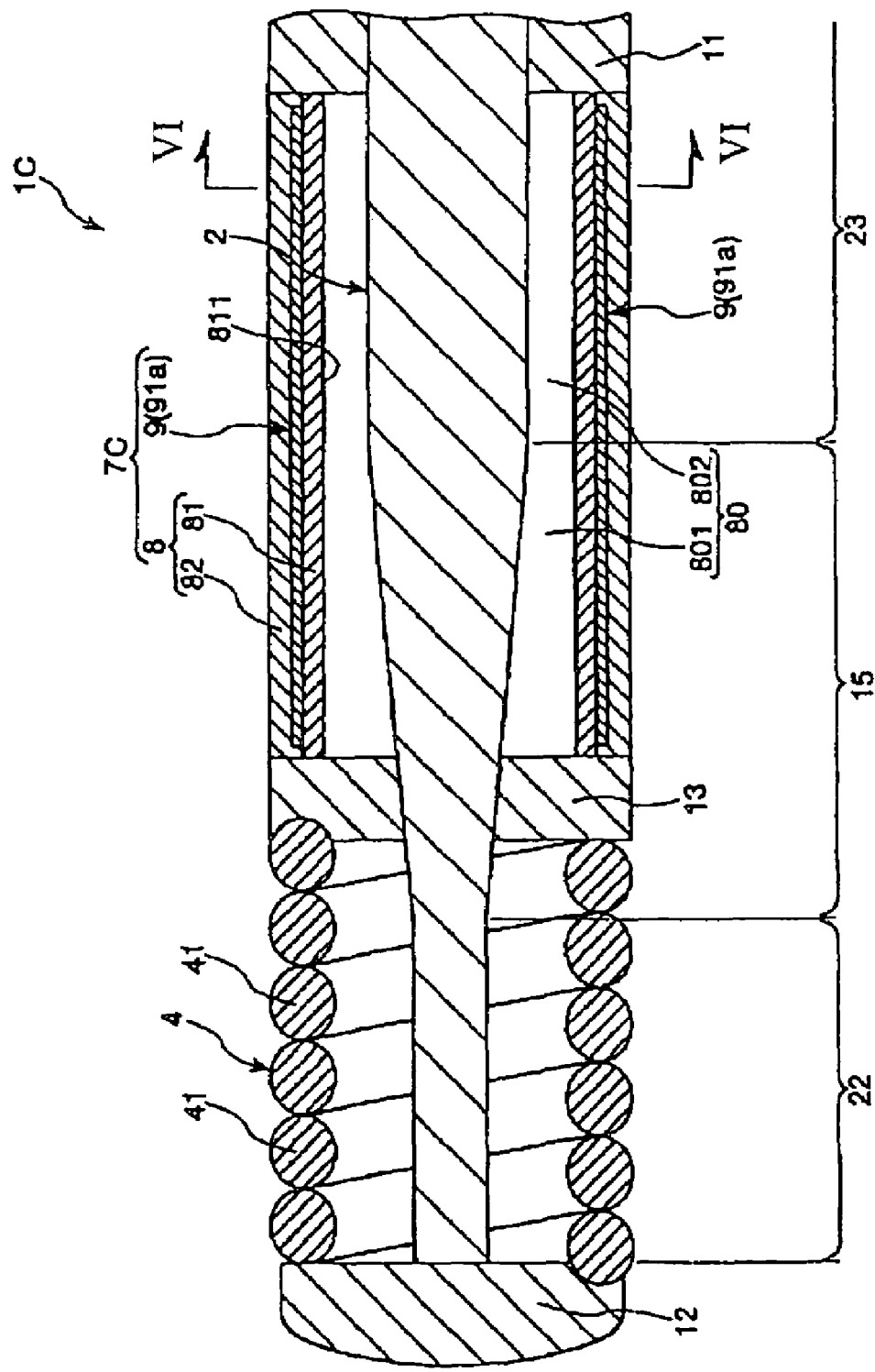
FIG. 5 is an enlarged detailed view of a distal end portion of a guide wire according to a fourth embodiment.
Figure 6:
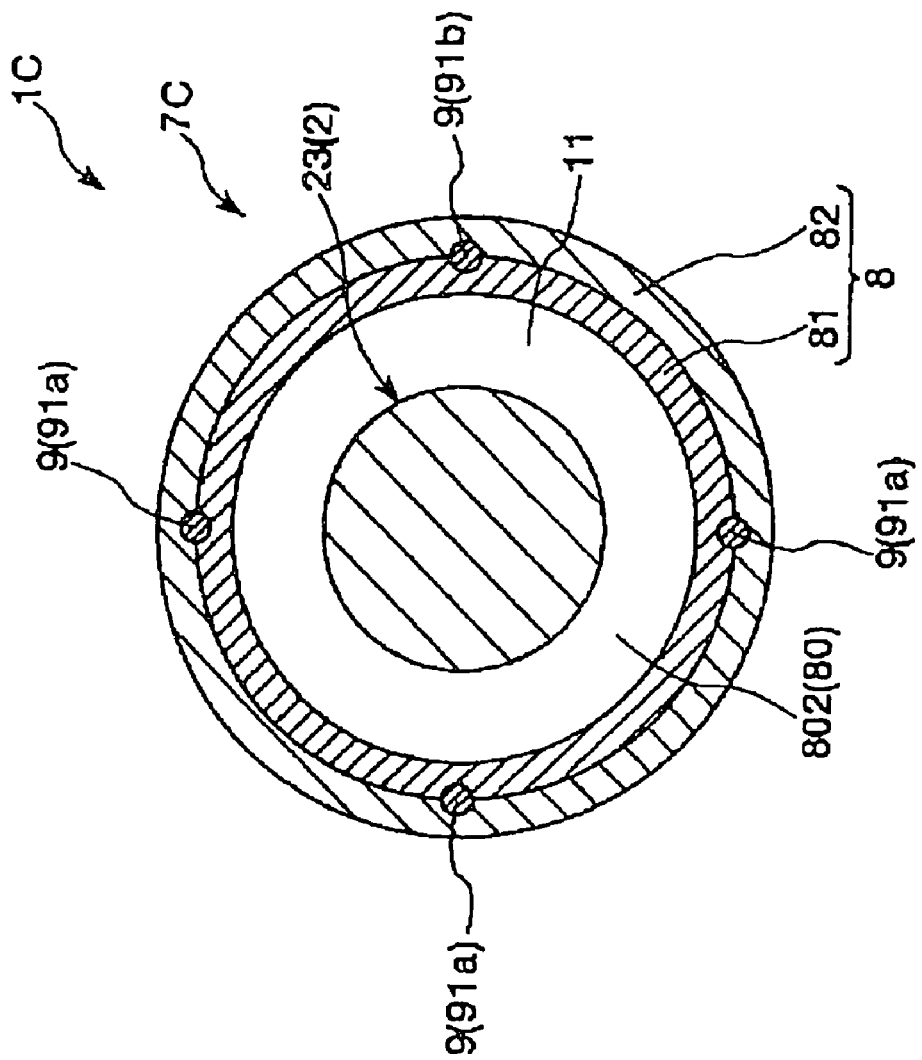
FIG. 6 is a sectional view taken along section line VI-VI in FIG. 5.

FIG. 5 illustrates the distal end portion of a guide wire according to a fourth embodiment, and FIG. 6 is a cross-sectional view taken along the section line VI-VI in FIG. 5. The description below of the guide wire according to this fourth embodiment will primarily discuss aspects of the guide wire different from those associated with the embodiments described above. Features of the fourth embodiment similar to those in the earlier embodiments are identified by the same reference numeral and a detailed description of such features is not repeated. This fourth embodiment is similar to the first embodiment described above, except that the fourth embodiment differs with respect to the formation state of the reinforcing member (wire-like member).

In the tubular member 7C of the guide wire 1C shown in FIG. 5, the reinforcing member 9 is formed from a wire material 91a having a linear configuration, and the wire material 91a is disposed along a longitudinal direction of the tubular member 7C.

Further, the tubular member 7C comprises four longitudinally extending and circumferentially spaced apart wire materials (wire members) 91a as shown in FIG. 6. The wire materials 91a are disposed intermittently in the circumferential direction of the tubular member at equal angular distances or intervals. The wire members or materials 91a are elongated and linear in extent.

With the guide wire 1C having the construction described above, the degree of rigidity of the tubular member 7C can be increased relative to, for example, the tubular member 7 in the first embodiment. Consequently, there is an advantage that the pushing-in property or the torque transmission property of the guide wire is enhanced.

The number of integrated or embedded wire materials 91a is not limited to four, but may be, for example, one, two, three, five, or more.

Though FIG. 6 illustrates the plurality of wire materials 91a disposed at equal angular intervals so that the installation density of the wire materials is equal in the circumferential direction of the tubular member 7C, the guide wire is not specifically limited to this arrangement. That is, the installation density of the wire materials 91a of the guide wire 1C is not limited to being equal, but may be non-uniform in arrangement so that circumferential portions vary in the density of the wire members or materials 91a.

Figure 7:
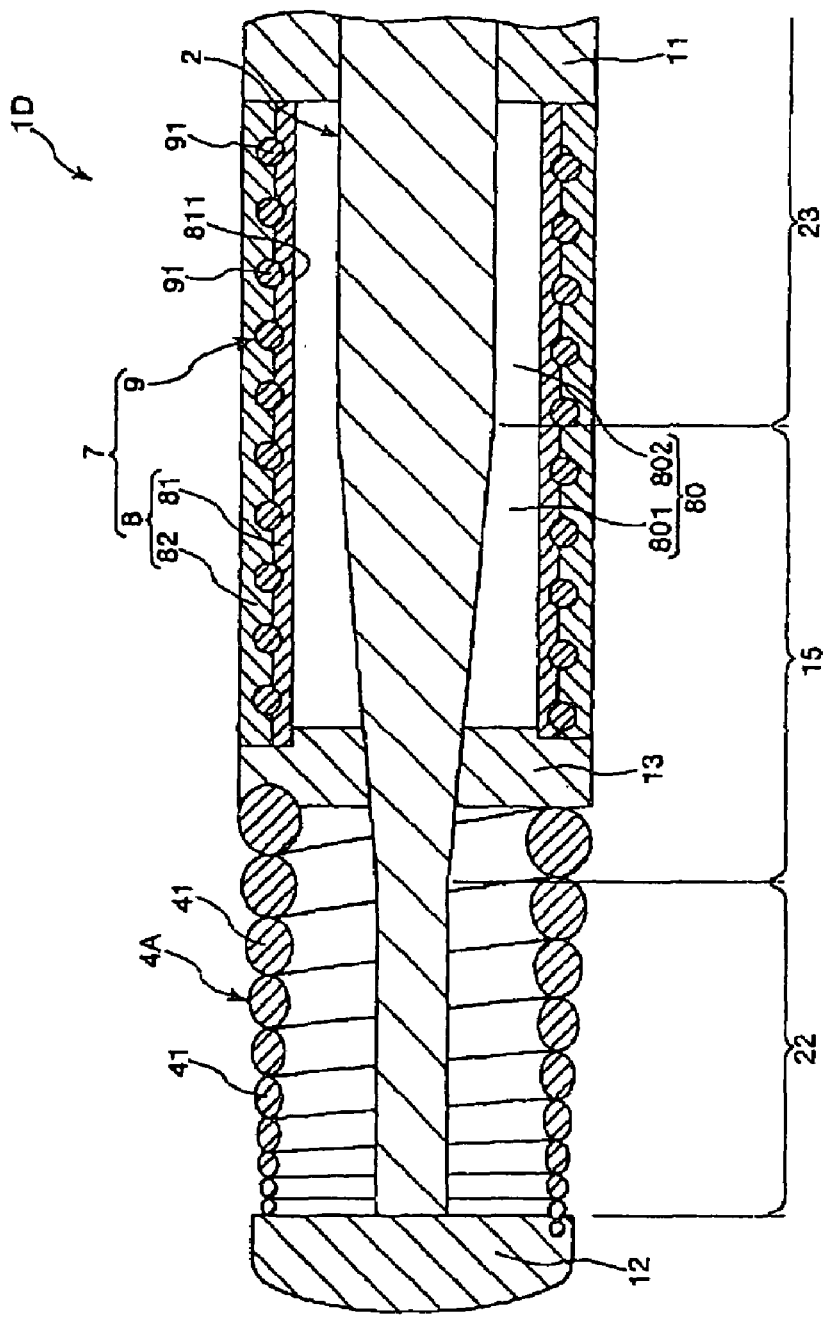
FIG. 7 is an enlarged detailed view of a distal end portion of a guide wire according to a firth embodiment.

FIG. 7 illustrates the distal end portion of a guide wire according to a fifth embodiment. The description below of the guide wire according to this fifth embodiment will primarily discuss aspects of the guide wire different from those associated with the embodiments described above. Features of the fifth embodiment similar to those in the earlier embodiments are identified by the same reference numeral and a detailed description of such features is not repeated. This fifth embodiment is similar to the first embodiment described above, except that the fifth embodiment differs in the outer shape of the coil.

The coil 4A of the guide wire 1D shown in FIG. 7 includes a wire member 41 whose wire diameter gradually decreases in the distal end direction. Together with this, the inner diameter and the outer diameter of the coil 4A also gradually decrease in the distal end direction.

In the guide wire 1D shown in GIG. 7, a relatively large space (clearance) exists between the inner surface of the coil 4A and the outer surface of the first wire 2 and so the guide wire 1D at this portion is more flexible.

Figure 8:
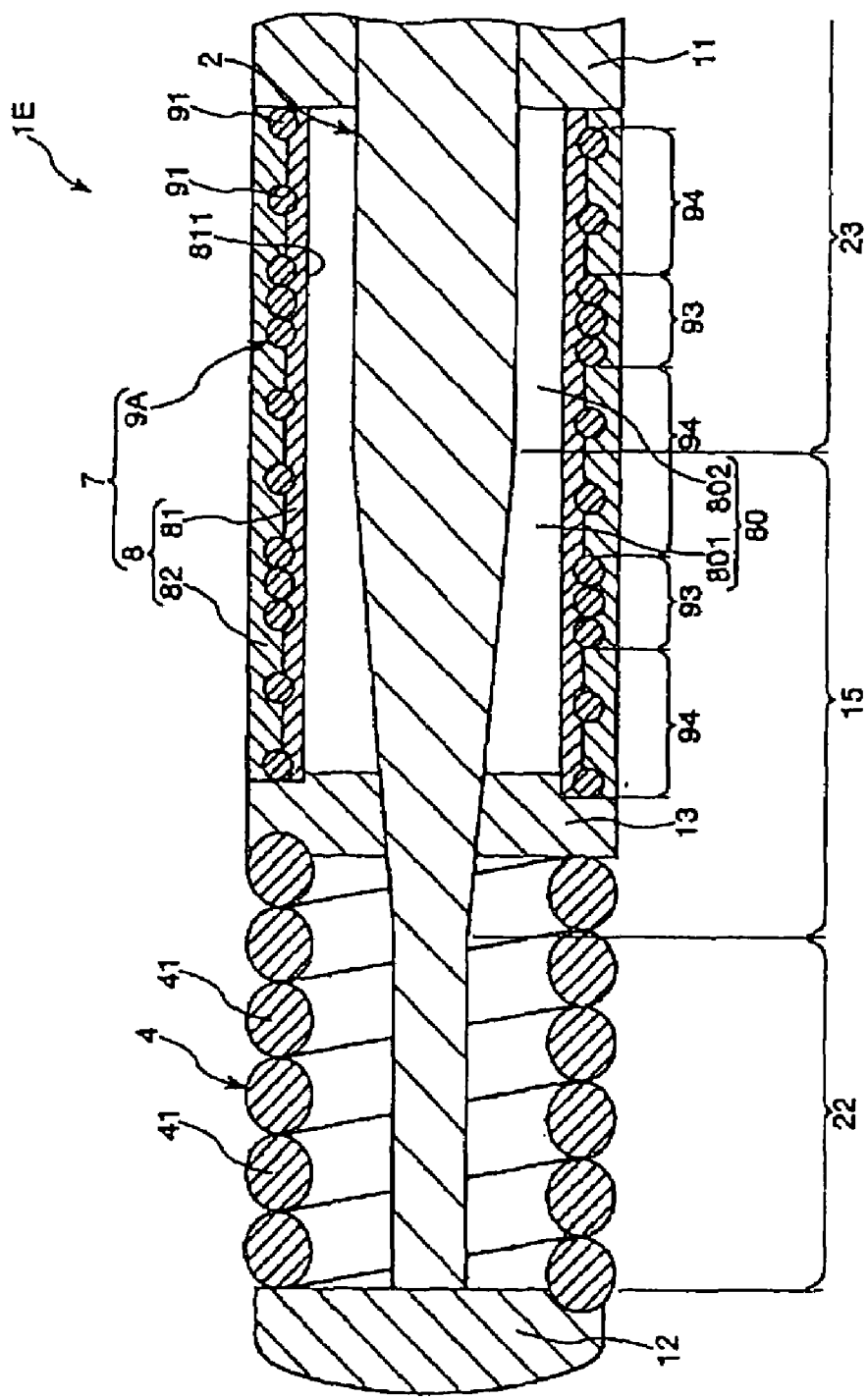
FIG. 8 is an enlarged detailed view of a distal end portion of a guide wire according to a sixth embodiment.

FIG. 8 illustrates the distal end portion of a guide wire according to a sixth embodiment. The description below of the guide wire according to this sixth embodiment will primarily discuss aspects of the guide wire different from those associated with the embodiments described above. Features of the sixth embodiment similar to those in the earlier embodiments are identified by the same reference numeral and a detailed description of such features is not repeated. This sixth embodiment is similar to the first embodiment described above, except that the sixth embodiment differs with respect to the formation state of the reinforcing member (wire-like member).

In the reinforcing member 9A of the guide wire 1E shown in FIG. 8, the winding density of the reinforcing member 9A differs in the longitudinal direction of the wire (along the longitudinal extent of the wire). In particular, the reinforcing member 9A includes a close winding portion 93 at which adjacent portions (windings) of the wire material 91 contact each other and a loose winding portion 94 at which adjacent portions (windings) of the wire material 91 are spaced away from each other. The close winding portions 93 and loose winding portions 94 are disposed in an alternating arrangement along the length of the wire as illustrated.

With the guide wire 1E having the construction shown in FIG. 8, the close winding portions 93 can be visually observed under radioscopy. As a result, by confirming a radioscopic image, the advancing situation of the guide wire 1E in a blood vessel or the like can be rather readily known and with a good degree of reliability. A reduction in the operation time and enhancement of the security can this be achieved.

In the guide wire 1E according to this embodiment, a loose winding portion 94 of a fixed length (for example, 1 to 2 cm) can be disposed between adjacent ones of a plurality of (for example 2 to 5) close winding portions 93. In this instance, by positioning the tubular member 7 (reinforcing member 9A) at a constricted portion of a blood vessel and using the close winding portions 93 as graduations under radioscopy, the length of the constricted portion can be determined.

While the guide wire of the present invention has been described above in connection with the embodiments shown in the drawings, the guide wire is not limited in this regard, and components of the guide wire can be replaced by those which can exhibit the same or similar functions. Further, additional components or features may be added.

Further, a guide wire can be configured to include a combination of aspects of two or more embodiments or a combination of configurations (features) of different embodiments described above.

For example, the exposed portion described above in connection with the second embodiment may be provided on the tubular member in the fourth embodiment.

Further, while the thickness of the wall of the tubular member is fixed along the wire longitudinal direction, it is not limited in this regard as the thickness may vary in the distal end direction.

The principles, embodiments and operational aspects of the guide wire disclosed here have been described in the foregoing specification, but the invention which is intended to be protected is not to be construed as limited to the particular embodiments disclosed. The embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

What is claimed is:

1. A guide wire comprising:
   an elongated flexible wire body possessing an outer surface;
   a tubular member disposed in covering relation to the outer periphery of a portion of the wire body on a distal end side of the wire body;
   the tubular member comprising a distal portion and a proximal portion;

the tubular member comprising a lamination portion and at least one wire member;

the lamination portion comprising an inner layer made of resin material and an outer layer made of resin material;

the at least one wire member being positioned between the inner layer and the outer layer;

the tubular member being fixed to the wire body;

the tubular member having an inner surface spaced from the outer surface of the wire body, with a gap between the inner surface of the tubular member and the outer surface of the wire body; and the gap between the inner surface of the tubular member and the outer surface of the wire body extending from the distal portion of the tubular member to the proximal portion of the tubular member.

2. The guide wire according to claim 1, wherein the wire member is a reinforcing member that reinforces the lamination portion.

3. The guide wire according to claim 2, wherein the reinforcing member comprises a distal-most end portion and a proximal-most end portion, the distal-most end portion of the reinforcing member being positioned distally of a distal-most end of the lamination portion so that the distal-most end portion of the reinforcing member is exposed outside the lamination portion and/or the proximal-most end portion of the reinforcing member being positioned proximally of a proximal-most end of the lamination portion so that the proximal-most end portion of the reinforcing member is exposed outside the lamination portion.

4. The guide wire according to claim 1, wherein the wire body possesses a distal end portion and a proximal end, the distal end portion of the wire body being a tapering portion in which an outer diameter of the tapering portion gradually decreases in a distal end direction, and the tapering portion possessing a proximal end that is axially positioned relative to the tubular member so that the proximal end of the tapering portion is encircled by the tubular member.

5. The guide wire according to claim 1, wherein the tubular member possesses a distal end that is fixed to the wire body by way of a fixing member that connects the wire body and the tubular member.

6. The guide wire according to claim 1, wherein the at least one wire member extends distally beyond the lamination portion, the wire member possessing a distal end that is fixed to the wire body by way of a fixing member that connects the wire body and the tubular member.

7. The guide wire according to claim 1, wherein the wire member is a helical coil.

8. The guide wire according to claim 7, wherein the helical coil comprises a plurality of adjacent windings, at least some of the adjacent windings being spaced from one another.

9. The guide wire according to claim 1, wherein the wire member comprises at least one linear wire member extending longitudinally along a longitudinal extent of the tubular member.

10. The guide wire according to claim 1, wherein the wire member comprises at plurality of linear wire members each extending longitudinally along a longitudinal extent of the tubular member.

11. The guide wire according to claim 9, wherein the plurality of linear wire members are circumferentially spaced apart from one another around a circumferential extent of the tubular member.

12. The guide wire according to claim 1, wherein the wire member of the tubular member possesses a distal end that extends distally beyond a distal end of the lamination portion so that the distal end of the wire member is exposed outside the lamination portion.

13. The guide wire according to claim 1, wherein the wire member of the tubular member possesses a proximal end that extends proximally beyond a proximal end of the lamination portion so that the proximal end of the wire member is exposed outside the lamination portion.

14. The guide wire according to claim 1, further comprising a coil positioned on a distal side of the tubular member and encircling a portion of the wire body, the coil comprising a spirally wound wire possessing an inner surface spaced from the outer periphery of the wire body.

15. The guide wire according to claim 14, wherein the at least one wire member possesses a wire diameter smaller than a wire diameter of the spirally wound wire forming the coil.

16. The guide wire according to claim 14, wherein the spirally wound wire forming the coil possesses a wire diameter that gradually decreases in a direction towards a distal end of the coil.

17. A guide wire comprising:

an elongated flexible wire body possessing an outer periphery;

the wire body possessing portions of different outer diameter;

the wire body possessing a distal end portion;

a tubular member disposed in covering relation to the outer periphery of the distal end portion of the wire body;

the tubular member comprising a distal portion and a proximal portion;

the tubular member being axially positioned relative to the wire body to cover portions of the wire body which possess different outer diameters;

the tubular member comprising a lamination portion made of resin material and a wire member;

the tubular member being fixed to the wire body;

the tubular member possessing an inner surface spaced from the outer periphery of the wire body with a gap between the inner surface of the tubular member and the outer periphery of the wire body;

the gap between the inner surface of the tubular member and the outer surface of the wire body extending from the distal portion of the tubular member to the proximal portion of the tubular member; and the wire member being embedded in the resin material forming the lamination portion so that inner and outer surfaces of at least a portion of a longitudinal extent of the wire member are covered by the resin material.

18. The guide wire according to claim 17, further comprising a coil positioned on a distal side of the tubular member and encircling a portion of the wire body, the coil possessing an inner surface spaced from the outer periphery of the wire body with a gap between the inner surface of the coil and the outer surface of the wire body.

19. The guide wire according to claim 17, wherein the wire member comprises a distal-most end portion and a proximal-most end portion, the distal-most end portion of the wire member being positioned distally of a distal-most end of the lamination portion so that the distal-most end portion of the wire member is exposed outside the lamination portion and/or the proximal-most end portion of the wire member being positioned proximally of a proximal-most end of the lamination portion so that the proximal-most end portion of the wire member is exposed outside the lamination portion.

20. A guide wire comprising:

an elongated flexible wire body possessing an outer surface;

a tubular member disposed in covering relation to the outer surface of a portion of the wire body on a distal end side of the wire body;

the tubular member comprising a distal portion and a proximal portion;

the tubular member comprising a resin material and a reinforcing member that reinforces the tubular member;

the tubular member being fixed to the wire body;

the tubular member having an inner surface spaced from the outer surface of the wire body, with a gap between the inner surface of the tubular member and the outer surface of the wire body; and the gap between the inner surface of the tubular member and the outer surface of the wire body extending from the distal portion of the tubular member to the proximal portion of the tubular member.

21. The guide wire according to claim 20, wherein the resin material comprises a lamination portion having an inner layer and an outer layer, the inner layer and outer layer being made of different materials, and the reinforcing member being disposed between the inner layer and the outer layer.

22. The guide wire according to claim 21, wherein the reinforcing member comprises a distal-most end portion and a proximal-most end portion, the distal-most end portion of the reinforcing member being positioned distally of a distal-most end of the lamination portion so that the distal-most end portion of the reinforcing member is exposed outside the lamination portion and/or the proximal-most end portion of the reinforcing member being positioned proximally of a proximal-most end of the lamination portion so that the proximal-most end portion of the reinforcing member is exposed outside the lamination portion.

23. The guide wire according to claim 20, wherein the reinforcing member comprises a helical coil.

24. The guide wire according to claim 20, wherein the reinforcing member comprises at least one linear wire extending longitudinally along a longitudinal extent of the tubular member.

25. The guide wire according to claim 20, wherein the reinforcing member comprises a plurality of linear wires each extending longitudinally along a longitudinal extent of the tubular member, the plurality of wires being circumferentially spaced apart from one another around a circumferential extent of the tubular member.

26. The guide wire according to claim 20, wherein the wire body possesses two axially spaced apart constant outer diameter portions and a taper portion disposed axially between the two constant outer diameter portions, each of the constant outer diameter portions possessing a constant outer diameter, and the taper portion possessing an outer diameter that tapers, the tubular member being axially positioned relative to the wire body such that the tubular member encircles at least a part of an axial extent of the taper portion.

27. The guide wire according to claim 20, further comprising a coil positioned on a distal side of the tubular member and encircling a portion of the wire body, the coil possessing an inner surface spaced from an outer surface of the wire body with a gap between the inner surface of the coil and the outer surface of the wire body.

\* \* \* \* \*